United States Patent
Kimura et al.

[11] Patent Number: 6,042,823
[45] Date of Patent: Mar. 28, 2000

[54] ENZYME COMPOSITION AND USE THEREOF

[75] Inventors: Shigeki Kimura; Tomonari Ogawa; Kinya Kariya, all of Aichi; Hideshi Yanase, Tottori, all of Japan

[73] Assignee: Amano Pharmaceuticals Co., Ltd., Aichi, Japan

[21] Appl. No.: 09/340,203

[22] Filed: Jun. 28, 1999

[30] Foreign Application Priority Data

Jul. 2, 1998 [JP] Japan ................................. 10-204293
Mar. 17, 1999 [JP] Japan ................................. 11-071122

[51] Int. Cl.⁷ .......................... A61K 38/51; A61K 38/54

[52] U.S. Cl. ..................................... 424/94.5; 424/94.2

[58] Field of Search .................................. 424/94.2, 94.5

[56] References Cited

U.S. PATENT DOCUMENTS

| | | | |
|---|---|---|---|
| 3,993,747 | 11/1976 | Gaffar et al. | 424/88 |
| 4,107,291 | 8/1978 | Ishibashi | 424/48 |
| 5,085,851 | 2/1992 | Okada et al. | 424/50 |
| 5,273,753 | 12/1993 | Ishihara et al. | 424/94.5 |
| 5,747,005 | 5/1998 | Barels et al. | 424/50 |

*Primary Examiner*—Raymond Henley, III
*Attorney, Agent, or Firm*—Sughrue, Mion, Zinn Macpeak & Seas, PLLC

[57] ABSTRACT

Oligosaccharides having physiological activities are synthesized in vivo in order to, for example, improve intestinal bacterial flora. An enzyme composition comprising an enzyme capable of forming an oligosaccharide having a physiological activity in the living body and a method for forming an oligosaccharide having a physiological activity in the living body are provided.

23 Claims, 4 Drawing Sheets

ENZYME COMPOSITION AND USE THEREOF

FIELD OF THE INVENTION

The present invention relates to an enzyme composition which comprises an enzyme capable of forming an oligosaccharide having a physiological activity in the living body and also relates to a method for forming an oligosaccharide having a physiological activity in the living body, which comprises using an enzyme composition.

BACKGROUND OF THE INVENTION

With the recent developments in studies to elucidate physiological actions and functions of carbohydrates, various useful saccharides have been found, and great concern has been directed particularly toward various oligosaccharides which are formed by glycosyltransferase, such as fructo-oligosaccharide, soy bean oligosaccharide, galacto-oligosaccharide, xylo-oligosaccharide, gentio-oligosaccharide, lactosucrose, coupling sugar and paratinose. Oligosaccharides are used not only as simple sweeteners but also as diet sweeteners by utilizing their anti-dental caries property or hardly digestible property to inhibit digestion and absorption of food as energy source. They are also used, for example, in foods for specified health use, with the aim of improving intestinal bacterial flora and improving physical conditions such as prevention of constipation or diarrhea and acceleration of peristalsis of the intestines, because they are used as nutrient sources by lactobacteria and bifidobacterium and can control intestinal environment, so that their physiological activities are drawing attention.

Oligosaccharides have been conventionally prepared by various methods. That is, they are produced in the industrial scale making use of various types of hydrolase, transferase, etc. As the method for supplying the oligosaccharides thus prepared into the living body, they are contained as the component in food materials such as carbonated drinks, soft drinks, table sugar, fermented milk, candies, biscuits and chocolate so as to exhibit their various physiological activities in the living body by the ingestion of such food materials, or these oligosaccharides are directly ingested.

However, when such various food materials are blended with these oligosaccharides, such application has many problems such as a high possibility of inhibiting taste, flavor and eating touch of the food materials and a necessity to select an oligosaccharide suited for each food material. In other words, positive ingestion of these oligosaccharides cannot satisfy the diversity of dietary life because of the necessity to selectively ingest a food material containing an oligosaccharide of interest.

SUMMARY OF THE INVENTION

The inventors of the present invention have made various studies on methods for supplying oligosaccharides into the living body. The present inventors have conducted extensive studies on the possibility of forming oligosaccharides in the living body and, as a result, found that formation of oligosaccharides in the living body can be achieved by ingesting an enzyme capable of acting in the living body together with a food material containing a substrate for forming oligosaccharides, thereby resulting in the accomplishment of the present invention.

Thus, the present invention relates to an enzyme composition comprising an enzyme capable of forming an oligosaccharide having a physiological activity in the living body.

The present invention further relates the above-described enzyme composition wherein said enzyme is capable of exerting its action in the stomach; the above-described enzyme composition wherein said enzyme catalyzes trans-glycosylation; the above-described enzyme composition wherein said enzyme is at least one enzyme selected from the group consisting of glucosyltransferase, fructosyltransferase and levansucrase; the above-described enzyme composition which further comprises at least one enzyme selected from the group consisting of amylase and invertase; and the above-described enzyme composition wherein said physiological activity is a diet effect.

The present invention also relates to a method for forming an oligosaccharide having a physiological activity in the living body, which comprises using any one of the above-described enzyme compositions. The present invention further relates to the above-described methods wherein the enzyme composition is taken before, between or after meals; and also relates to the method wherein the enzyme composition is taken together with food.

DETAILED DESCRIPTION OF THE INVENTION

Figure 1:
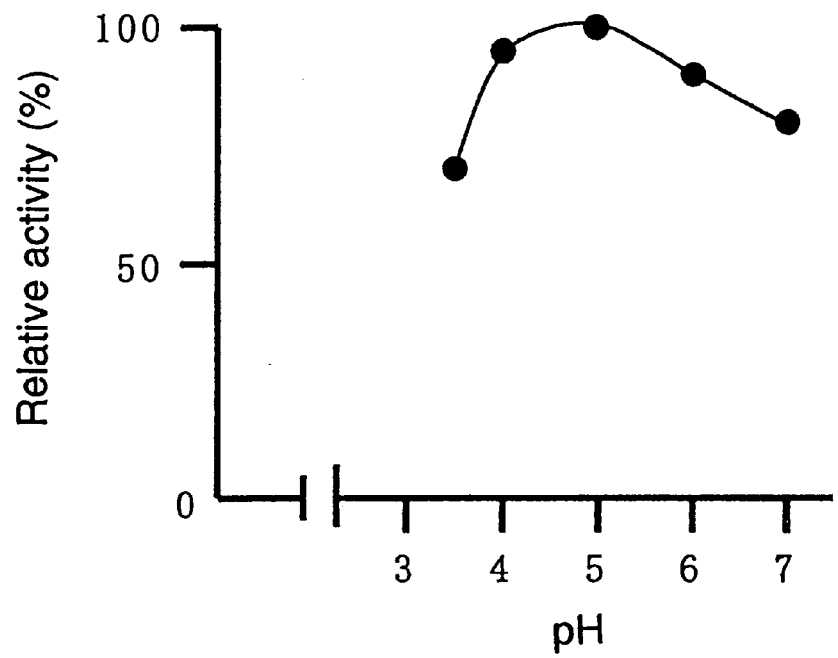
FIG. 1 is a graph showing a result of Example 1, regarding the influence of pH on the enzymatic action of glucosyltransferase.

Regarding the enzyme which can exert its action in the living body and also can synthesize an oligosaccharide in the living body by acting upon a substrate component ingested as a food material, any enzyme can be used with as long as it can exert its action in the environment of the living body.

Examples of the aforementioned oligosaccharides having various physiological activities include fructo-oligosaccharides (those in which 1 to 3 fructose molecules are linked to the fructose residue of sucrose at the C2- and C1-positions by β-bonding), branched oligosaccharides (oligosaccharides having α-1,6 bond), galacto-oligosaccharides (such as raffinose and stachyose) and gentio-oligosaccharides (oligosaccharides having β-1,6-glucoside bond), and their more illustrative examples include 4-α-glucosyl-xylose, 3-α-glucosyl-sorbose, 4-α-glucosyl-sucrose, 4-α-glucosyl-mannose, 4-α-glucosyl-glucosamine, 4-α-glucosyl-N-acetyl-glucosamine, 3-,6-α-glucosyl-mannose, 3-,4-α-glucosyl-xylose, 1-,3-,4-α-glucosyl-fructose, α-glucosyl-glycerol, riboflavin-α-glucoside, 6-α-galactosyl-fructose, 6-α-galactosylgalactose, α-galactosyl-glycerol, 3-,4-,6-β-galactosyl-lactose, β-galactosyl-glycerol, 4-β-galactosyl-glucose, 4-β-galactosyl-mannose, β-galactosyl-glycerol, xylosyl-fructoside, galactosyl-fructoside, isomaltosyl-fructoside, lactosyl-fructoside, 1-kestose, nistose (fructo-oligosaccharide), neokestose, inulobiose, difructofuranosyl 1,2':2,1':2,3':2,6':2'6-dianhydride and lactosucrose.

These hetero-oligosaccharides can be synthesized making use of various types of glycosyltransferase. Examples of the glycosyltransferase include those having actions to transfer glucosyl group, galactosyl group and fructosyl group. Transglucosidase, cyclodextrin synthetase, amylomaltase, α-glucosidase and β-glucosidase are known as the enzymes which can be used for glucosyl group transfer; α-galactosidase, β-galactosidase and β-galactanase are known as the enzymes which can be used for galactosyl group transfer; and levansucrase, β-fructofuranosidase and a cyclic disaccharide synthetase can be used for fructosyl group transfer.

For example, 4-α-glucosyl-xylose, 3-α-glucosyl-sorbose and 4-α-glucosyl-sucrose can be synthesized making use of cyclodextrin synthetase; 4-α-glucosyl-mannose, 4-α-glucosyl-glucosamine and 4-α-glucosyl-N-acetyl-glucosamine can be synthesized making use of amylomaltase; 3-,6-α-glucosyl-mannose, 3-,4-α-glucosyl-xylose, 1-,3-,4-α-glucosyl-fructose, α-glucosyl-glycerol and riboflavin-α-glucoside can be synthesized making use of α-glucosidase; 6-α-galactosyl-fructose, 6-α-galactosyl-galactose, α-galactosyl-glycerol, 3-,4-,6-β-galactosyl-lactose and β-galactosyl-glycerol can be synthesized making use of α-galactosidase; 4-β-galactosyl-glucose, 4-β-galactosyl-mannose and β-galactosyl-glycerol can be synthesized making use of β-galactosidase; xylosyl-fructoside, galactosyl-fructoside, isomaltosyl-fructoside and lactosyl-fructoside can be synthesized making use of levansucrase; 1-kestose, nistose (fructo-oligosaccharide), neokestose, inulobiose, xylosyl-fructoside and galactosyl-fructoside can be synthesized making use of β-fructofuranosidase; and difructofuranosyl 1,2':2,1':2,3':2,6':2'6-dianhydride can be synthesized making use of a cyclic disaccharide synthetase.

Though formation of oligosaccharides by these reactions can be expected by mere administration of these transferases when components to be used as their substrates are sufficiently present in the food material, it is desirable and more effective to include other enzymes, such as amylase and invertase, which can act upon the food material and thereby produce components to be used as the substrates of these transferases.

Regarding the origin of the aforementioned enzymes to be used, any origins such as bacteria, fungi, yeast, actinomycetes, basidiomycetes, plants and animals may be useful, but, when actions of these enzymes are required in the living body, particularly in the stomach, their deactivation at low pH range in the stomach becomes a problem, so that it is necessary to select enzymes which can exert sufficiently stable effects at low pH.

Regarding examples of the enzymes which can be used in the present invention, glucosyltransferase is an enzyme which has a function to form isomaltose, panose and other oligosaccharides by transferring glucose, and its known origins include microorganisms such as the genus Streptococcus, the genus Bacillus, the genus Aspergillus, the genus Aureobasidium and the genus Klebsiella and plants such as onion. More illustratively, *Aspergillus niger* glucosyltransferase (trade name: Transglucosidase L "Amano", manufactured by Amano Pharmaceutical Co., Ltd.) can be used.

Fructosyltransferase is an enzyme which has a function to act mainly upon sucrose to cut β-1,2 bond between fructose and glucose and then transfer the fructose released to sucrose to produce oligosaccharides, and its known origins include microorganisms such as the genus Bacillus, the genus Arthrobacter, the genus Aspergillus, the genus Fusarium, the genus Gloeosporium, the genus Saccharomyces, the genus Rhodotorula, the genus Pichia, the genus Hansenula and the genus Candida and plants such as asparagus and Jerusalem artichoke. More illustratively, Bacillus natto fructosyltransferase can be exemplified [*Denpun Kagaku,* vol. 38, no. 2, 217–222 (1991)].

Levansucrase is an enzyme which transfers fructose moiety of sucrose to produce various oligosaccharides such as a high molecular weight polysaccharide levan, and its examples include *Zymomonas mobilis* IFO-13756 levansucrase [*Journal of Fermentation and Bioengineering,* vol. 79, no. 4, 367–369 (1995)] and *Rahnella aquatilis* JCM-1683 enzyme.

Amylase is an enzyme which acts upon starch to produce disaccharides, trisaccharides and oligosaccharides that are substrates of the glycosyltransferase, and *Aspergillus oryzae* amylase (trade name: Biodiastase 2000, manufactured by Amano Pharmaceutical Co., Ltd.) can be cited as its more illustrative example.

According to the present invention, these enzymes may be administered to the living body in combination with food material components to be used as their substrates, separately with the food material or simultaneously therewith, but, in order to obtain effective actions of these enzymes in the living body, it is important to design a place where these enzymes can coexist with food materials which become their substrates.

In general, the food taken from the mouth is digested through complex steps. In the ordinary case, it is hydrolyzed firstly by α-amylase secreted from the salivary gland, secondary by pepsin in the stomach under hydrochloric acid acidic condition and finally in the intestines by various enzymes secreted from the pancreas and then absorbed from the intestinal wall as nutrient substances.

In consequence, when effects of oligosaccharides having physiological activities are expected, it is desirable that these oligosaccharides are formed at the initial stage of digestive tracts, namely it is desirable that these oligosaccharides are purified by the reaction of enzymes with various substrates under the acidic environment in the stomach.

In order to obtain effective actions of the simultaneously ingested enzyme composition of the present invention in the stomach after ingestion of food into the living body, enzymes which constitute the composition should have such properties that they can sufficiently act under the acidic condition of the stomach. Because of this, the *Aspergillus niger* glucosyltransferase (trade name: Transglucosidase L "Amano", manufactured by Amano Pharmaceutical Co., Ltd.), *Zymomonas mobilis* IFO-13756 levansucrase and *Aspergillus oryzae* amylase (trade name: Biodiastase 2000, manufactured by Amano Pharmaceutical Co., Ltd.) can be cited as particularly preferred components among the aforementioned enzymes.

Regarding the dose of the enzyme composition, it may be such an amount that the oligosaccharide forming actions are exerted in the living body, but it may greatly vary depending on the properties and purity of each enzyme to be used, so that it is necessary to set the dose in response to respective properties. For example, the desirable dose may be from 10,000 to 5,000,000 units/once in the case of the aforementioned glucosyltransferase, from 100 to 50,000 units/once for levansucrase or from 10 to 5,000 units/once for amylase.

In addition, as occasion demands, these enzymes can be made into an enzyme composition by blending them with other effective components taking the problem of incompatibility into consideration. As a matter of course, various auxiliaries can also be blended for preparation of the composition. It is possible also to combine it with an antacid or jointly use an agent acting on the digestive tract (e.g., $H_2$ blocker).

Regarding the method for administering the enzyme composition to the living body to effect its action upon the substrate as a food component, the composition can be used in any dosage form such as powders, granules, solutions, solids or capsules. Also, in order to ingest the enzyme composition simultaneously with food materials, it may be used by mixing with various components. Illustratively, it can be ingested simultaneously with a meal for example by mixing it with sucrose in the coating of corn flakes.

The above-described enzyme composition or the like can be administered generally from one to three times per day to a subject such as warm blooded animals, preferably mammals, more preferably human. The amount of oligosaccharides to be formed in the living body is about 2 g/day to 5 g/day. The intended physiological activities of the oligosaccharides includes improvement of intestinal bacterial flora, prevention of constipation or diarrhea and acceleration of peristalsis of the intestines, and diet (body weight control such as prevention of adiposis).

Examples of the present invention are given below by way of illustration and not by way of limitation.

In this connection, unless otherwise noted, respective enzyme activities were measured by the following method.

Glucosyltransferase Activity

Using α-methyl-D-glucoside as the substrate, the enzyme solution is allowed to undergo its reaction at 40° C. and at pH 5.0, and amount of the enzyme which produces 1 μg of glucose during 60 minutes is defined as one unit.

Levansucrase Activity

Measured using the F Kit (D-glucose/D-fructose) (manufactured by Boehringer-Mannheim GmbH). Using sucrose as the substrate, amount of the enzyme which produces 1 mg/ml of glucose in the reaction solution is defined as one unit.

Amylase Activity

Measured in accordance with the method for testing starch saccharification activity (37° C., pH 5), among the digestion activity testing methods described in *The Pharmacopoeia of Japan* (General Test Methods). Amount of the enzyme which increases a reducing power equivalent to 1 mg of glucose within 1 minute is defined as one unit.

EXAMPLE 1

Using *Aspergillus niger* glucosyltransferase (trade name: Transglucosidase L "Amano", manufactured by Amano Pharmaceutical Co., Ltd.), *Zymomonas mobilis* IFO-13756 levansucrase [*Journal of Fermentation and Bioengineering*, vol. 79, no. 4, 367–369 (1995)] and *Aspergillus oryzae* amylase (trade name: Biodiastase 2000, manufactured by Amano Pharmaceutical Co., Ltd.) as the enzymes to be tested, effects of pH on their enzyme actions were examined.

Test Method (pH stability of enzymes)

Figure 2:
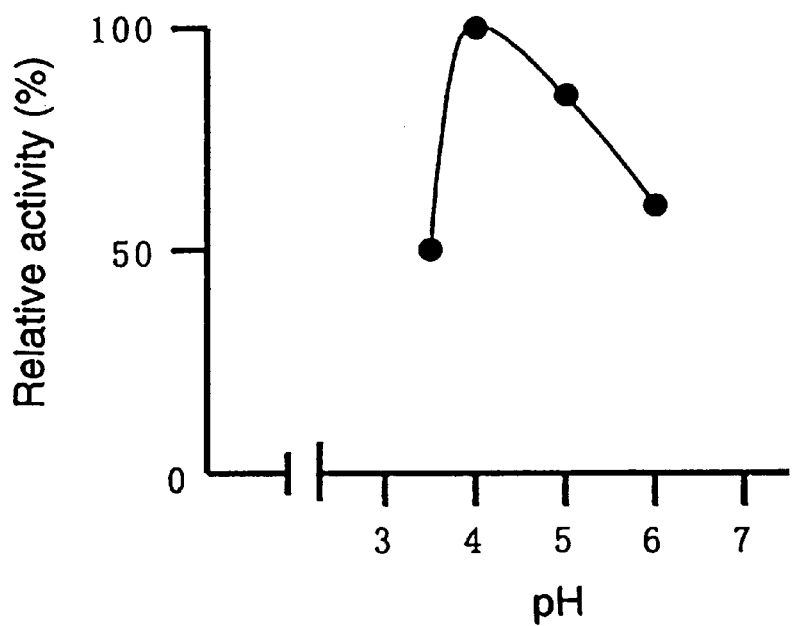
FIG. 2 is a graph showing a result of Example 1, regarding the influence of pH on the enzymatic action of levansucrase.
Figure 3:
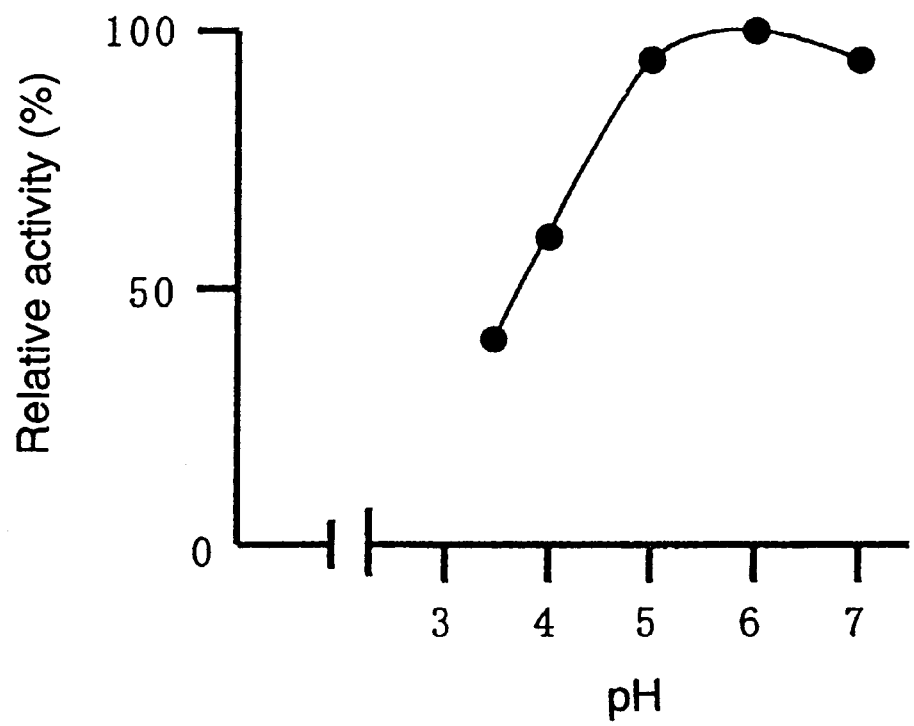
FIG. 3 is a graph showing a result of Example 1, regarding the influence of pH on the enzymatic action of α-amylase.

Each enzyme in a buffer solution having respective pH value was treated at 37° C. for 1 hour to measure the residual activity, and the results were expressed as relative values to the highest activity which was defined as 100%. The results are shown in FIGS. 1 to 3.

All of the tested enzymes showed sufficient residual activity at a pH value of from 3.5 to 6, thus confirming that these enzymes have properties which can be applied to the reaction in the stomach.

EXAMPLE 2

Using a digestive tract model, a transfer reaction was carried out by allowing the levansucrase described in Example 1 to act upon sucrose and lactose as its substrates.

The substrate solution was prepared by adding 6.86% of sucrose, 3.01% of lactose, 0.1% of gastric mucosa mucin, 150 mM of $Na^+$ and 1 mM of $Ca^+$ to 13 mM acetate buffer (pH 4) containing 0.067 mg/ml of pepsin and adjusting the final pH to 4.0 with hydrochloric acid.

Gastric model: While maintaining the above-described substrate solution at 37° C., the reaction was carried out by adding 500 units of levansucrase under gently stirring, and 0.1N hydrochloric acid was added at intervals of 15 minutes until 70 minutes after the commencement of reaction. The period until 120 minutes after the commencement of reaction was used as the gastric environment. Thereafter, the reaction system was used as an intestinal model by adding sodium bicarbonate, sodium taurodeoxycholate and pancreatic enzymes. A portion of the contents was sampled during the reaction, mixed with hydrochloric acid to terminate the reaction and then subjected to HPLC analysis.

Figure 4:
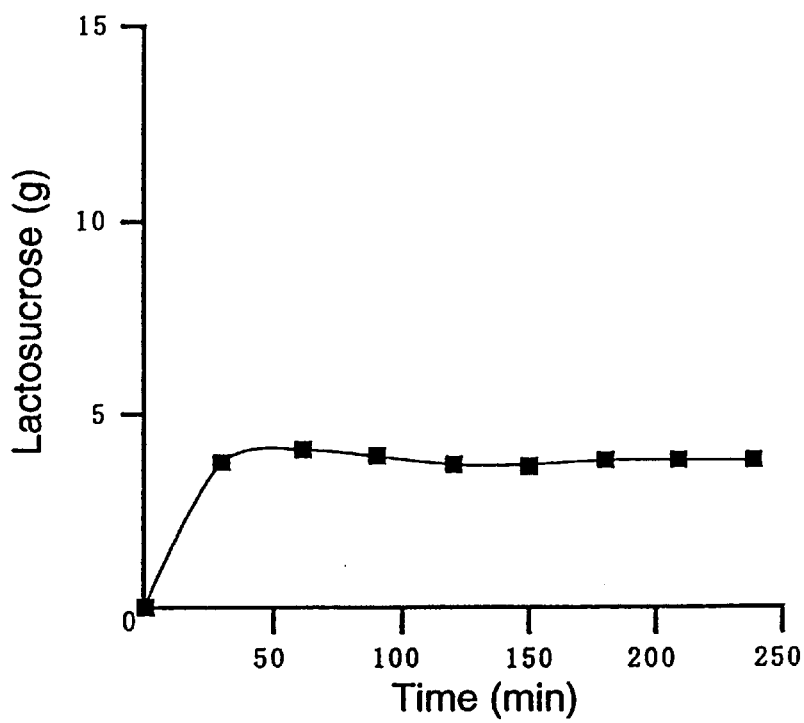
FIG. 4 is a graph showing results of Example 2.

The results are shown in FIG. 4. It was confirmed from the results that lactosucrose was formed under the gastric environment.

EXAMPLE 3

Using a digestive tract model in the same manner as described in Example 2, formation of oligosaccharides was measured by the reaction of amylase, transglucosidase and levansucrase.

The substrate solution (150 ml) consisted of dextrin (Pinedex: PD #100), 6.86%, of sucrose, 3.01% of lactose, 0.1% of gastric mucosa mucin, 150 mM of $Na^+$, 1 mM of $Ca^+$ and 13 mM of acetate buffer (pH 4), which was adjusted to the final pH of 4.0 with hydrochloric acid.

Gastric model: While maintaining the just described substrate solution at 37° C., the reaction was carried out by adding 10 mg of pepsin, 70 mg of Biodiastase, 100,000 units of transglucosidase and 500 units of levansucrase under gently stirring, and 0.1N hydrochloric acid was added at intervals of 15 minutes until 70 minutes after the commencement of reaction. The period until 120 minutes after the commencement of reaction was used as the gastric environment. Thereafter, the reaction system was used as an intestinal model by adding sodium bicarbonate, sodium taurodeoxycholate and pancreatic enzymes. A portion of the contents was sampled during the reaction, mixed with hydrochloric acid to terminate the reaction and then subjected to HPLC analysis.

Figure 5:
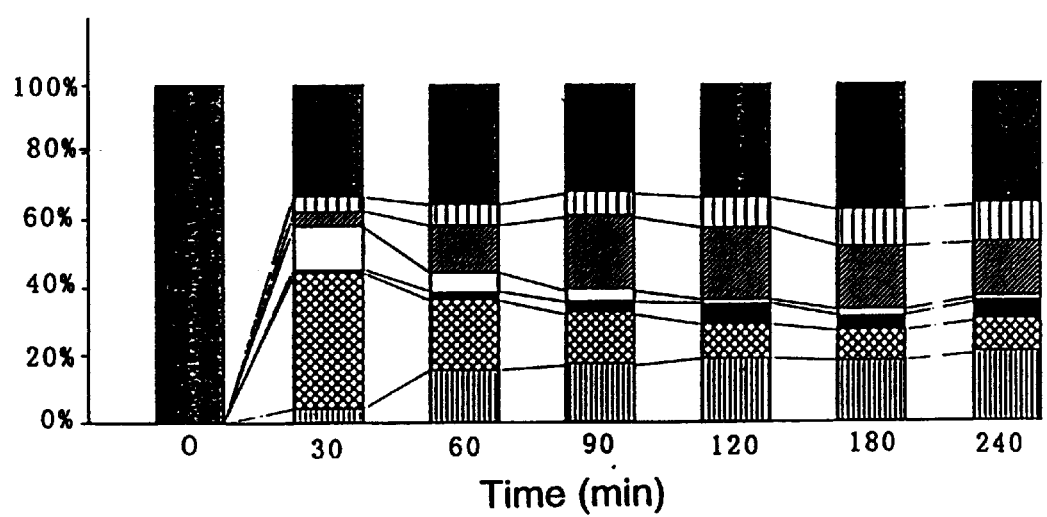
FIG. 5 is a graph showing results of Example 3, in which saccharides formed are shown in the order of glucose, maltose, isomaltose, maltotriose, panose, lactosucrose and other saccharides by their ratios starting from the bottom.

The results are shown in FIG. 5. It was confirmed from the results that various oligosaccharides such as isomaltose, panose and lactosucrose were formed under the gastric environment.

From this result, it is clear that 2 to 5 g of oligosaccharides which is considered to be an effective amount per day can be sufficiently formed from the substrates in foods.

EXAMPLE 4

When the procedure of Example 1 was repeated except for using β-fructofuranosidase instead of levansucrase, formation of lactosucrose was found.

EXAMPLE 5

The following enzyme composition was administered to seven healthy adults having low ratio of the bifidobacterium content, after each meal for 14 days. In this case, the meals were freely given without particular limitation.

| | |
|---|---|
| Amylase | 5 parts |
| Transglucosidase | 5 parts |
| Levansucrase | 5 parts |
| Filler (lactose) | 53 parts |
| Binder (crystalline cellulose) | 30 parts |
| Fluidizing agent (soft silicic anhydride) | 1 part |
| Lubricant (magnesium stearate) | 1 part |

The mixture of above composition was made into tablets in the usual way, and three tablets were administered after each meal.

Bifidobacterium cells in the feces were measured, with the results shown in Table 1. Each of the data shown indicates the average of logarithmic values of the number of bifidobacterium cells in 1 g of three fece samples of each adults. As the results, significant increase in the number of bifidobacterium cells was found in five adults feces, and defecation was improved in all adults tested.

TABLE 1

| | Before | After 14 days |
|---|---|---|
| 1 | 8.8 | 9.7* |
| 2 | 7.5 | 8.8* |
| 3 | 8.2 | 9.0* |
| 4 | 9.1 | 9.2 |
| 5 | 8.3 | 8.9* |
| 6 | 8.5 | 8.4 |
| 7 | 7.8 | 9.3* |

*Significant increase

In other words, it is considered that administration of the enzyme composition at the time of meals induced in vivo formation of oligosaccharides from various components contained in food, these oligosaccharides promoted growth of bifidobacterium, and the resulting acetic acid and lactic acid accompanied by the proliferation of bifidobacterium improved intestinal flora by inhibiting growth of intestinal toxic bacteria and promoted the movement of intestines by inhibiting formation of putrefactive products in the intestines.

EXAMPLE 6

Basal composition of feed

| | |
|---|---|
| Mixed feed (New Koromeal GS: manufactured by Nippon Formula Feed Mfg.) | 150 g |
| Dextrin | 35 g |
| Sucrose | 10 g |
| Lactose | 5 g |

First group: Basal composition feed plus levansucrase (85 mg), Biodiastase (140 mg) and transglucosidase (310 mg)

Second group: Basal composition feed plus levansucrase (85 mg)

Third group: Basal composition feed alone

Pigs of about 7 kg in body weight were fed for 7 days with the basal composition feed alone and then divided into animals per group and fed with the above respective feed for 14 days. Weight gain per day and the number of bifidobacterium cells in the intestines were measured, with the results shown in Tables 2 and 3. Each of the data shown in Table 3 indicates the average of logarithmic values of the number of bifidobacterium cells in 1 g of intestinal contents of pigs in each group.

TABLE 2

| | Weight gain (g/day) |
|---|---|
| First group | 59.3 ± 16.6 |
| Second group | 59.4 ± 30.9 |
| Third group | 76.5 ± 15.5 |

TABLE 3

| | Cecum | Ascending colon | Descending colon | Rectum |
|---|---|---|---|---|
| First group | 7.9 | 8.4 | 8.8 | 8.1 |
| Second group | 7.3 | 7.5 | 7.8 | 7.8 |
| Third group | <6.0 | 6.9 | 7.5 | 7.6 |

As is evident from the above tables, weight gain in pigs was definitely controlled by the use of the enzyme composition of the present invention, in comparison with the case of pigs fed with the usual feed, and propagation of bifidobacterium in the intestines was confirmed also by its use. In other words, it is considered that such effect to prevent adiposis and increase of useful intestinal bacterium are caused by the formation of hardly digestible oligosaccharides in the living body effected by the enzyme composition of the present invention. From this result, it is believed that the enzyme composition of the present invention when used for diabetes patients can suppress formation and absorption of blood sugar increasing components in food and thus suppress blood sugar increase.

EXAMPLE 7

Using corn flakes and milk, a test on the formation of oligosaccharides in a gastric model was carried out in the following manner. Milk (200 ml) was added to and mixed with 40 g of Corn Flosty (trade name), and the mixture was stirred at 37° C. for 30 minutes and then adjusted to pH 4.5±0.2. In accordance with the procedure of Example 1, an enzyme composition of the following formulation was added to and dissolved in 10 ml of the above-described system.

| (1) | Levansucrase | 50 mg |
| --- | --- | --- |
| (2) | Levansucrase | 50 mg |
|  | Transglucosidase | 183 mg |
|  | Biodiastase-2000 | 250 mg |

Figure 6:
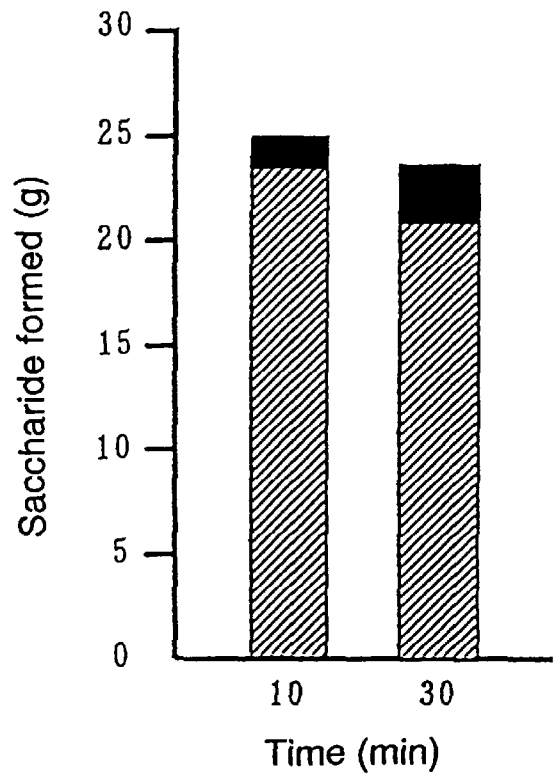
FIG. 6 is a graph showing a result of Example 7, in which saccharides formed are shown as the total amounts of other saccharides and oligosaccharides in this order starting from the bottom.
Figure 7:
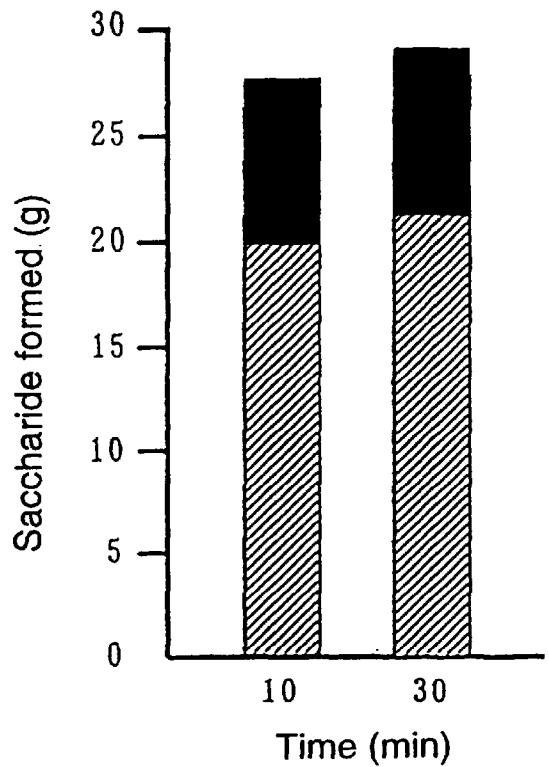
FIG. 7 is a graph showing another result of Example 7, in which formed saccharides are shown as the total amounts of other saccharides and oligosaccharides in this order starting from the bottom.

Samples were taken out after 10 and 30 minutes of the reaction and subjected to centrifugation (3,000 rpm, 5 minutes) with cooling, and then a 1 ml portion of the resulting supernatant was mixed with 1 ml of 50 mM $Na_2CO_3$-$NaH_2PO_4$ (pH 9.0) to terminate the reaction. A 0.01 ml portion of the reaction-terminated solution was mixed with 0.29 ml of water and 0.7 ml of acetonitrile, and the mixture was filtered and subjected to liquid chromatography analysis. The results are shown in FIGS. 6 and 7. As is evident from these drawings, oligosaccharides having physiological activities are formed by the use of the enzyme composition of the present invention after 10 minutes and 30 minutes of the reaction.

By the action of the enzyme composition provided by the present invention, oligosaccharides having physiological activities are formed from components ingested as enzyme substrates into the living body through food, so that it is possible, for example, to improve intestinal flora by effective actions of the formed oligosaccharides upon the living body. The present invention renders possible the utilization of oligosaccharides useful for the living body without being particularly conscious of their use, so that diet effect and also an effect to suppress blood sugar increase in diabetes patients can be obtained.

While the invention has been described in detail and with reference to specific embodiments thereof, it will be apparent to one skilled in the art that various changes and modifications can be made therein without departing from the spirit and scope thereof.

This application is based on Japanese patent applications No. Hei.-10-204293, filed on Jul. 2, 1998, 1998 and No. Hei.-11-71122, filed on Mar. 17, 1999, both incorporated herein by reference.

What is claimed is:

1. An enzyme composition comprising a first enzyme and at least one additional enzyme, selected from the group consisting of amylase and invertase, capable of forming an oligosaccharide having a physiological activity in the living body.

2. The enzyme composition according to claim 1, wherein said enzymes are capable of exerting their action in the stomach.

3. The enzyme composition according to claim 1, wherein said first enzyme catalyzes transglycosylation.

4. The enzyme composition according to claim 1, wherein said first enzyme is at least one enzyme selected from the group consisting of glucosyltransferase, fructosyltransferase and levansucrase.

5. The enzyme composition according to claim 1, wherein said physiological activity is an effect to prevent adiposis.

6. The enzyme composition according to claim 1, wherein said physiological activity is an effect to suppress blood sugar increase in diabetes patients.

7. A method of forming a physiologically active oligosaccharide in a living body comprising administrating to a subject an effective amount of an enzyme composition comprising an enzyme capable of forming, in the living body, a physiologically active oligosaccharide.

8. A method of preventing adiposis comprising administrating to a subject an effective amount of an enzyme composition comprising an enzyme capable of forming, in the living body, a physiologically active oligosaccharide.

9. A method of controlling weight gain comprising administrating to a subject an effective amount of an enzyme composition comprising an enzyme capable of forming, in the living body, a physiologically active oligosaccharide.

10. A method of inhibiting growth of intestinal toxic bacteria comprising administrating to a subject an effective amount of an enzyme composition comprising an enzyme capable of forming, in the living body, a physiologically active oligosaccharide.

11. A method of inhibiting the formation of putrefactive products in an intestine comprising administrating to a subject an effective amount of an enzyme composition comprising an enzyme capable of forming, in the living body, a physiologically active oligosaccharide.

12. A method of preventing constipation or diarrhea comprising administrating to a subject an effective amount of an enzyme composition comprising an enzyme capable of forming, in the living body, a physiologically active oligosaccharide.

13. A method of suppressing an increase in blood sugar comprising administrating to a subject an effective amount of an enzyme composition comprising an enzyme capable of forming, in the living body, a physiologically active oligosaccharide.

14. A method of treating diabetes comprising administrating to a subject an effective amount of an enzyme composition comprising an enzyme capable of forming, in the living body, a physiologically active oligosaccharide.

15. The method according to claim 7, 8, 9, 10, 11, 12, 13, or 14 wherein said enzyme is capable of exerting its action in the stomach.

16. The method according to claim 7, 8, 9, 10, 11, 12, 13, or 14 wherein said enzyme catalyzes transglycosylation.

17. The method of according to claim 7, 8, 9, 10, 11, 12, 13, or 14 wherein said enzyme is at least one enzyme selected from the group consisting of glucosyltransferase, frutosyltransferase and levansucrase.

18. The method according to claim 17 wherein the glucosyltransferase is administered in an amount of 10,000 to 5,000,000 units.

19. The method according to claim 17 wherein the levansucrose is administered in an amount of 100 to 50,000 units.

20. The method according to claim 7, 8, 9, 10, 11, 12, 13, or 14 which further comprises administering at least one enzyme selected from the group consisting of amylase and invertase.

21. The method according to claim 20 wherein the amylase is administered in an amount of 10 to 5,000 units.

22. The method according to claim 7, 8, 9, 10, 11, 12, 13, or 14 wherein said enzyme composition is taken before, between or after meals.

23. The method according to claim 7, 8, 9, 10, 11, 12, 13, or 14 wherein said enzyme composition is taken together with food.

* * * * *